(12) United States Patent
Fink et al.

(10) Patent No.: US 8,037,945 B2
(45) Date of Patent: Oct. 18, 2011

(54) ATOMIC FORCE MICROSCOPE WITH COMBINED FTIR-RAMAN SPECTROSCOPY HAVING A MICRO THERMAL ANALYZER

(75) Inventors: Samuel D. Fink, Aiken, SC (US); Fernando F. Fondeur, North Augusta, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 541 days.

(21) Appl. No.: 12/082,572

(22) Filed: Apr. 12, 2008

(65) Prior Publication Data

US 2011/0113516 A1  May 12, 2011

Related U.S. Application Data

(60) Provisional application No. 60/923,252, filed on Apr. 13, 2007.

(51) Int. Cl.
*G01B 5/28* (2006.01)
(52) U.S. Cl. .................................. 173/105; 116/275
(58) Field of Classification Search ............ 73/105; 116/275
See application file for complete search history.

(56) References Cited

U.S. PATENT DOCUMENTS

| | | | |
|---|---|---|---|
| 5,171,992 A | 12/1992 | Clabes et al. | |
| 7,608,818 B2* | 10/2009 | Miller et al. | 250/288 |
| 2002/0048610 A1* | 4/2002 | Cima et al. | 424/725 |
| 2003/0162226 A1* | 8/2003 | Cima et al. | 435/7.1 |
| 2005/0191614 A1* | 9/2005 | Cima et al. | 435/4 |
| 2006/0153269 A1 | 7/2006 | Lakestani et al. | |

OTHER PUBLICATIONS

Fritz Keilmann; Vibrational-infrared near-field microscopy; Vibrational Spectroscopy 29 (1-2); 2002; pp. 109-114; Elsevier Science B.V. Germany; (6 pages).

Mark S. Anderson and Stephen D. Gaimari; Raman-atomic force microscopy of the ommatidial surface of dipteran compound eyes: Journal of Structural Biology 142:2003; pp. 364-368; Elsevier Science United States; (5 pages).

Michael Reading et al; Micro-Thermal Analysis of Polymers: Current Capabilities and Future Prospects; Macomol. Symp.: 2001; pp. 45-62; Wiley-Vch Verlag GmbH, Weinheim (18 pages).

\* cited by examiner

*Primary Examiner* — Hezron E Williams
*Assistant Examiner* — Rodney T Frank
(74) *Attorney, Agent, or Firm* — J. Bennett Mullinax, LLC

(57) ABSTRACT

An atomic force microscope is provided that includes a micro thermal analyzer with a tip. The micro thermal analyzer is configured for obtaining topographical data from a sample. A raman spectrometer is included and is configured for use in obtaining chemical data from the sample.

19 Claims, 3 Drawing Sheets

US 8,037,945 B2

ATOMIC FORCE MICROSCOPE WITH COMBINED FTIR-RAMAN SPECTROSCOPY HAVING A MICRO THERMAL ANALYZER

CROSS REFERENCE TO RELATED APPLICATION

This application claims the benefit of U.S. Application Ser. No. 60/923,252 filed on Apr. 13, 2007 and entitled, "Atomic Force Microscope with Combined FTIR-Raman Spectroscopy Having a Micro Thermal Analyzer." U.S. Application Ser. No. 60/923,252 is incorporated by reference herein in its entirety for all purposes.

STATEMENT AS TO RIGHTS TO INVENTIONS MADE UNDER FEDERALLY SPONSORED RESEARCH AND DEVELOPMENT

This invention was made with Government support under Contract No. DE-AC09-96-SR18500 awarded by the United States Department of Energy. The Government has certain rights in the invention.

FIELD OF THE INVENTION

The present invention relates generally to an atomic force microscope for obtaining information from a sample. A particular exemplary embodiment of the present application is related to combining an atomic force microscope, in the form of a microthermal analyzer, with infra-red spectroscopy and Raman spectroscopy analyzers for multiple simultaneous analyses. Another exemplary embodiment is related to containing the atomic force microscope and associated probes within an enclosure that allows the user to control a gas environment around the sample to thereby study selected chemical behavior.

BACKGROUND

An atomic force microscope is a device capable of imaging samples at the nanoscale level. The atomic force microscope typically includes a cantilever that has an extremely small radius of curvature. A tip extends from the cantilever and may be placed into contact with a sample being examined or may be spaced from the sample depending upon the specific testing scheme. In contact mode, the tip is placed against the sample and drug across its outer surface. A laser is reflected off of a portion of the top of the cantilever usually opposite the tip. The reflected laser light is then directed onto an array of photodiodes. Stimulation of different photodiodes results in data that can be processed to develop a three dimensional image of the surface of the sample.

As stated, atomic force microscopes are also arranged so that the tip extending from the cantilever is positioned some distance from the sample. Here, an electron cloud circling the tip interacts with an electron cloud at the surface of the sample to cause the tip to be repelled. The cantilever can be externally oscillated at a known phase, frequency and amplitude. Certain systems focus a laser onto the tip in order to generate these known parameters. The interaction between the surface and the tip will cause the phase, frequency and amplitude of the cantilever to be different than that at which it was originally motivated. These differences can be measured and yield information about various characteristics of the sample. Atomic force microscopes are capable of measuring contact forces, electrostatic forces and magnetic forces of the sample and can also provide topographic data as previously indicated.

Chemical bonds which make up the surface of the sample vibrate at different energy levels depending upon the shape of their molecular surfaces, their mass, and the type of exhibited coupling. Infrared light applied to the surface will be absorbed at different wavelengths depending upon the arrangement of bonds present. Multiple wavelengths of infrared light can be measured through use of a Fourier transform to create a graph of wavelength absorption. From this information the types of bonds present may be deduced to then result in an identification of the chemical composition of the surface.

Atomic force microscopes are also arranged to provide data regarding both topography and thermal conductivity of a sample. For example, one such atomic force microscope employs a tip that is a thermal resistor. Current is passed through the tip as it is moved over the sample. The amount of current needed to maintain the tip at a constant temperature is measured to result in a thermal conductivity map of the surface of the sample. At the same time, the topography of the surface can be measured so that this data is acquired in addition to the calorimetric properties.

Although various atomic force microscopes are known for acquiring different types of data from samples, prior atomic force microscopes are limited in that a particular system cannot provide certain combinations of data. Accordingly, there remains room for variation and improvement within the art.

SUMMARY

Various features and advantages of the invention will be set forth in part in the following description, or may be obvious from the description, or may be learned from practice of the invention.

The present invention provides for an atomic force microscope that includes a micro thermal analyzer with a tip. A sample is received on a base so that the sample and tip are capable of relative movement with respect to one another. An infrared light generator is present and capable of directing an infrared beam onto the tip. A laser is also present and can direct a laser beam onto the micro thermal analyzer. A photodiode array receives the directed laser beam from the micro thermal analyzer and communicates this information to a microprocessor. Topographic information, thermal information and molecular species information of the sample can be calculated by the atomic force microscope. An enclosure that surrounds the sample when the sample is placed onto the base may also be included. The enclosure acts to contain a gas therein to which the sample is exposed during analysis.

These and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGS. in which.

Figure 1:
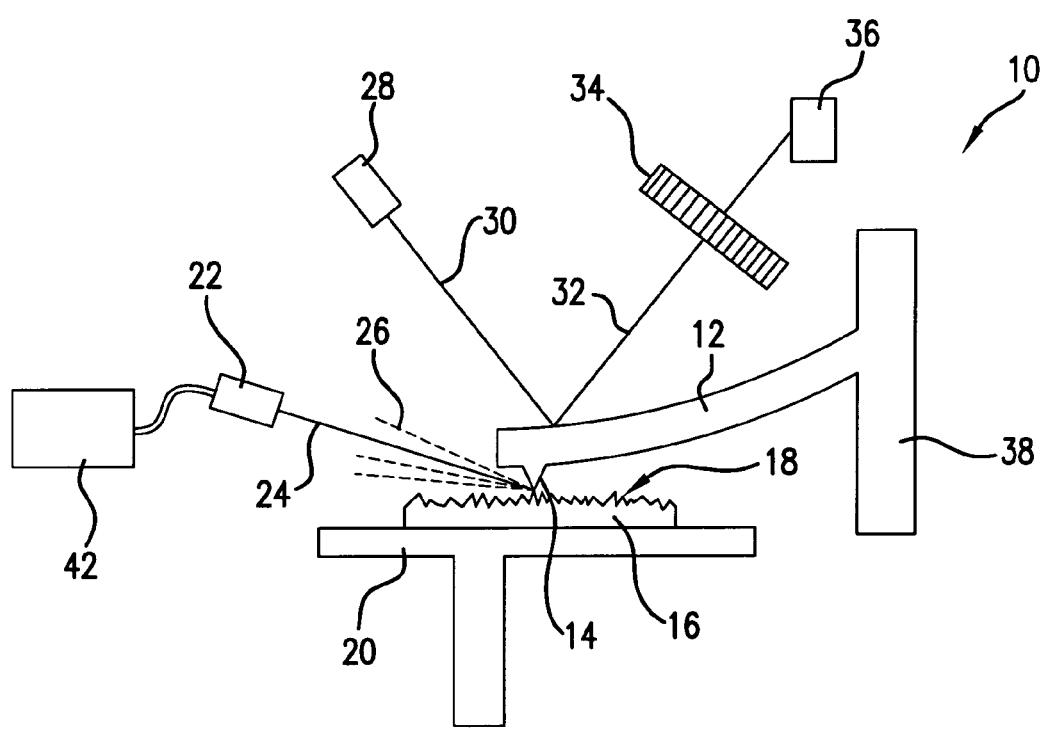
FIG. 1 is a schematic view of an atomic force microscope arrangement in accordance with one exemplary embodiment of the present invention that uses an infrared source and analyzer.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an atomic force microscope 10 that includes a micro thermal analyzer 12 for obtaining calorimetric data from a sample 16. In this regard, the enthalpy and heat capacity of the sample 16 can be determined. The atomic force microscope 10 may also be capable of obtaining topographic information from the sample 16, and the atomic force microscope 10 operating in conjunction with an FTIR spectroscopy 40 and/or a Raman spectroscopy unit 42 may identify the molecular species of the sample 16 to determine the chemical composition of the surface 18 and of the sample 16. The hyphenated instrument measures the chemical evolution of the locally heated area as the local area is heated. The atomic force microscope tip 14 and the sample 16 and sample stage 20 may be located inside a gas tight enclosure 44 that allows the user to alter the gas 46 present and study chemical interactions or reactions' of the sample 16 with selected gases 46. The atomic force microscope 10 may be configured for optimum versatility by being a single system capable of obtaining calorimetric data, topographical data and chemical data of the sample 16.

An atomic force microscope 10 in accordance with one exemplary embodiment of the present invention is shown in FIG. 1. Here, the atomic force microscope 10 includes a probe that is a micro thermal analyzer 12. The micro thermal analyzer 12 is a curved cantilever that extends from a wall 38 of the atomic force microscope 10. The micro thermal analyzer 12 can have any radius of curvature commonly known in the art with respect to other cantilevers on atomic force microscopes. In some configurations of atomic force microscope 10, the resolution of the topographical image obtained of the sample 16 is limited by the radius of curvature of the cantilever. A tip 14 extends from one side of the curved cantilever of the micro thermal analyzer 12. The tip 14 can be made of a variety of materials in accordance with certain exemplary embodiments of the present invention. For example, the tip 14 can be made of gold, silver or platinum. The tip 14 can have a generally conical, solid shape that is sized on the order of nanometers.

A sample stage (also referred to as a base) 20 is included onto which a sample 16 to be studied is positioned. The atomic force microscope 10 is capable of analyzing an area of the sample 16 that is generally on the order of 150 micrometers by 150 micrometers. In a similar manner, the height of the sample 16 that is studied is usually on the order of micrometers. The tip 14 is placed proximate to the surface 18 of the sample 16 when acquiring information about the sample 16. Additionally or alternatively, the atomic force microscope 10 can operate in contact mode in which the tip 14 is placed into contact with the surface 18. Measurement of the position of the micro thermal analyzer 12 is made in order to determine the position of the tip 14 with respect to the surface 18. Relative movement between the tip 14 and surface 18 and corresponding measurement of the position of the micro thermal analyzer 12 enables a topographic image of the surface 18 to be generated.

The position of the micro thermal analyzer 12 can be determined in a number of ways. One such method makes use of a laser 28. As shown, a laser 28 emits a laser beam 30 onto the portion of the micro thermal analyzer 12 opposite tip 14. A reflected laser beam 32 is then directed onto a photodiode array 34. The reflected laser beam 32 can activate different portions of the photodiode array 34 in order to provide information as to the position of the tip 14 and thus the height of the surface 18 of sample 16. Data from the photodiode array 34 can be directed to a microprocessor 36 for processing and use in constructing a three dimensional map of the surface 18 of sample 16.

The atomic force microscope 10 in accordance with one exemplary embodiment of the present invention may have the added capability of locally heating the sample 16 and monitoring the temperature of the heated area. The micro thermal analyzer 12 may provide the amount of heat given off and/or taken in by the heated area as the temperature of the heated area is increased. In accordance with one exemplary embodiment, the temperature is increased from ambient to 450° C. In accordance with another exemplary embodiment of the present invention the temperature is increased from 15° C. to 450° C.

The atomic force microscope 10 also includes an infrared light generator 22. In accordance with one exemplary embodiment, the infrared light generator 22 is a fiber optic that emits an infrared beam (and/or an infrared laser from a quantum cascade laser) 24 with a wavelength range of 2000 to 200 nm. It is to be understood, however, that in other exemplary embodiments the wavelength of infrared beam 24 can be varied. For example, the wavelength of infrared beam 24 may be from 400 nm to 1200 nm in accordance with other embodiments of the present invention. The infrared light generator 22 directs infrared beam 24 onto the tip 14. Contact with the tip 14 causes infrared beam 24 to scatter thus resulting in infrared scattering 26. The infrared beam 24 acts to heat the surface 18 of sample 16 proximate to tip 14. This process results in modulated temperatures of the surface 18 proximate to tip 14 as well as fluctuations in the shape of surface 18 due to expansion and contraction from the application of infrared beam 24.

Figure 2:
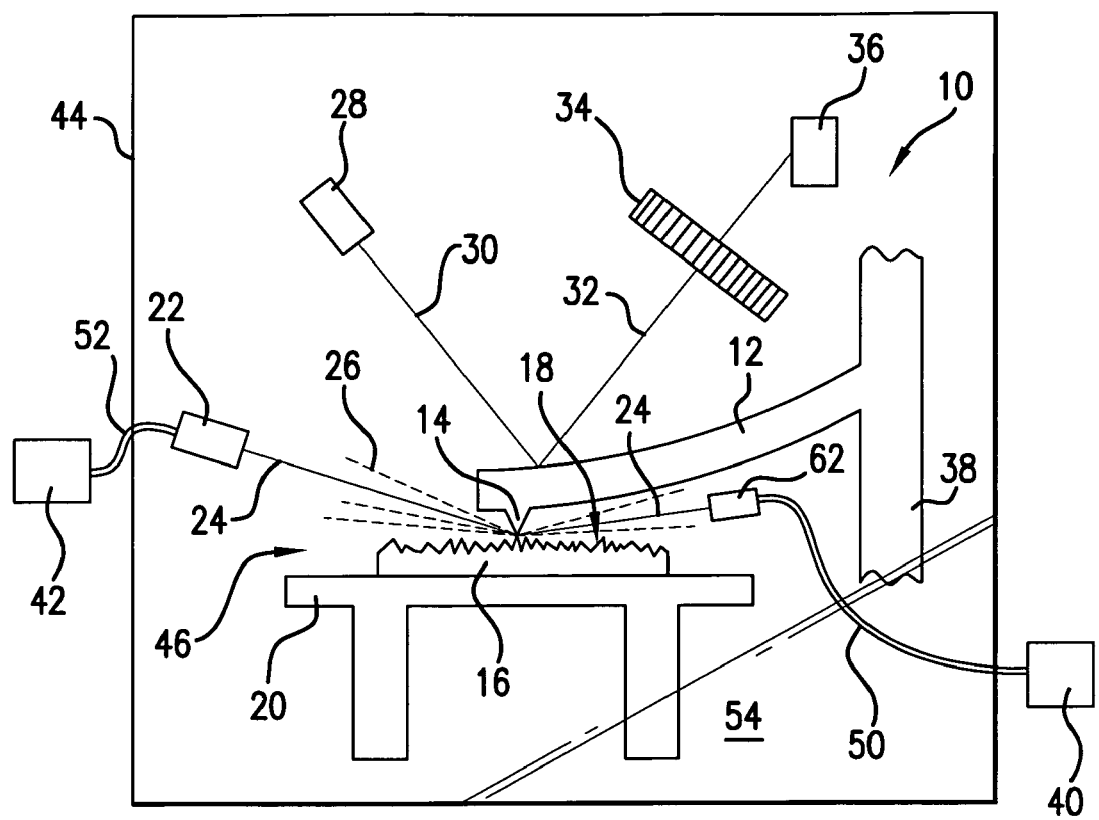
FIG. 2 is a schematic view of an atomic force microscope arrangement in accordance with another exemplary embodiment of the present invention that uses combined Raman and infrared spectral sources and analyzers.

The atomic force microscope 10 can be used to determine the chemical composition of the sample 16. Chemical bonds that make up the surface 18 and bulk of sample 16 vibrate at energy levels depending upon the shape of their molecular surfaces, their mass, and the type of exhibited coupling. Application of infrared beam 24 to surface 18 causes a certain amount of infrared light to be absorbed at different wavelengths depending upon the particular bonds present. The vibration of the bonds can be measured through the perturbed motion of the vibrating atomic force needle. As the molecules on the surface absorb heat, their vibrations interact with the air molecules generating acoustical pulses that interact with the vibrating atomic force needle. A Fourier analysis of the microthermal analyzer needle 14 motion reveals the molecular vibration responsible for the acoustical wave and therefore, a chemical identification of the molecules on the surface can be made. This method will detect molecules with polar (permanent dipoles) groups. Similarly, the microthermal analyzer needle 14 can read the surface temperature resulting from the heating and cooling of the surface 18 due to the infrared 24 absorption. The measured heat from the needle 14 contains information on the chemical composition of the surface 18. Heat generated through application of the infrared beam 24 is collected with an infrared transparent optical fiber 50 from a sensor 62 as shown in FIG. 2. Multiple wavelengths of infrared light 24 can be measured through use of a Fourier transform to create a graph of wavelength absorption. From this information the types of bonds present may be deduced to then result in an identification of the chemical composition of the surface 18. The atomic force microscope 10 can thus be used, for example, to identify hydrogen, organic material and inorganic material on mineral surfaces 18.

In accordance with one exemplary embodiment of the present invention, the tip 14 is placed into contact with the surface 18 of sample 16 and infrared beam 24 is directed onto tip 14. Here, the infrared light generator 22 is a heated lamp (and/or quantum cascade laser) delivered by a fiber optic to the atomic force needle-sample area. The atomic force microscope 10 includes a fiber optic Fourier Transform Infrared (FTIR) spectrometer 40 that will collect the infrared light emitted by the heated surface 18. Such a spectrometer 40 may be obtained from Remspec Corporation having offices at 6 City Depot Road, Charlton, Mass., or alternatively may be a NEXUS® 670 produced by Thermo Electron Corporation having offices at 81 Wyman Street, Waltham, Mass. The spectrometers 40 and 42 may include a photodiode array, microprocessor, infrared light generator, and a detector for sensing infrared heat. The temperature of surface 18 of sample 16 will modulate with the same frequency as the radiation emitted by the heated surface 18 to the FTIR spectrometer 40.

The micro thermal analyzer 12 in contact with surface 18 of sample 16 may measure the temperature of the surface 18 through detecting movement of the surface 18 due to the applied infrared beam 24. Alternatively, the micro thermal analyzer 12 acts as a thermocouple to contact the surface 18 and measure its temperature. The infrared scattering 26 may stimulate various photodiodes resulting in a signal which is Fourier transformed in order to yield the vibrational spectrum of the contact area between tip 14 and surface 18. The vibrational spectrum is subsequently used to determine the enthalpy and heat capacity of the sample 16.

Other thermal properties, such as thermal conductivity, of the sample 16 are also capable of being ascertained by the atomic force microscope 10. The micro thermal analyzer can have a tip 14 that is made of or includes a resistive thermal member. The thermal member can be used to collect thermal conductivity data of the sample 16 through noting the amount of current needed to maintain the thermal member at a selected temperature. Measurements of thermal properties such as thermal diffusivity may be performed using processes similar to those found in U.S. Patent Application Publication U.S. 2006/0153269 entitled "Method and System for Measuring the Thermal Diffusivity." The entire contents of U.S. Patent Application Publication U.S. 2006/0153269 are incorporated herein in their entirety for all purposes.

Another exemplary embodiment of the present invention exists in an atomic force microscope 10 that is set up the same as that previously discussed. However, in this exemplary embodiment, the surface 18 of sample 16 is heated with the micro thermal analyzer 12. In this regard, an electrical current can be passed through tip 14 into surface 18 to cause an amount of heating until the surface 18 is heated to a desired temperature. The FTIR spectrometer 40 can collect a fraction of the heat given off by the sample 16. In this regard, an infrared transparent optical fiber can be placed near the contact area of surface 18 to collect heat given off from the heated sample 16. This heat is decoded by the FTIR spectrometer 40 to reveal molecules with permanent dipoles and derive the chemical make-up of surface 18. The heat is Fourier transformed by the FTIR spectrometer 40 to yield the vibrational spectrum of the sample 16 from which calorimetric data such as enthalpy and heat capacity can be obtained.

In another exemplary embodiment, the surface 18 of sample 16 is heated with the micro thermal analyzer 12. A fraction of the heat radiating from the sample surface 18 is collected by placing an infrared transparent optical fiber 62 close to the contact area. The heat is decoded by the FTIR spectrometer 40 to reveal the molecules with permanent dipoles and determine the chemical composition of the sample surface 18 as the surface is heated to high temperatures. The chemical information obtained from this exemplary embodiment will provide insights into the sample thermal transformation during heating.

Yet another exemplary embodiment of the present invention is found in an atomic force microscope 10, shown in FIG. 2, in which a laser 22, which can be a 785 nm wavelength laser, directs a laser beam 24 onto the tip 14/surface 18 contact area. The laser beam scatters from the atomic force tip to generate an enhanced laser light field that interacts with the molecules on the surface. The enhanced laser light will scatter from the molecules and generate the Raman effect. The fiber optics collects the scattered laser light that contains the Raman effect from the atomic force needle and a Fourier transform is conducted to reveal the molecules on the surface responsible for the Raman effect. The micro thermal analyzer 12 can then be configured to cyclically heat the sample 16 by altering the applied AC current thus resulting in expanding and contracting of the surface 18 with the heating cycle. The micro thermal analyzer 12 includes AC circuitry that allows the tip 14 to obtain an elevated temperature and then cyclically heated to a yet hotter temperature while reading the sample 16 temperature between the heating. The atomic force microscope 10 includes a fiber optic spectrometer 42 such as a Raman spectrometer 42 produced by Kaiser Optical Systems, Inc., having offices at 371 Parkland Plaza, Ann Arbor, Mich. 48103. The fiber optic spectrometer 42 is in communication with the micro thermal analyzer 12 through the use of a fiber optic cable 52. A FTIR spectroscopy unit 40 is also included and is placed into communication with the micro thermal analyzer 12 by way of a fiber optic cable 50. The micro thermal analyzer 12 and fiber optic cables 50 and 52 are located behind a viewing window 54 included in a rectangular containment. Sample 16 is located on a base 20 that forms a three dimensional stage that brings the sample 16 into contact with tip 14.

The area of surface 18 that expands and contracts due to the heat applied by the micro thermal analyzer 12 will be limited to that between tip 14 and surface 18 proximate to tip 14. The reflection of infrared beam 24 at the contact area will change direction upon the cyclical expansion and contraction. The fiber optic spectrometer 42 will receive power fluctuations that are surges and drops from the infrared scattering 26. The modulated fiber optic scattering received by the fiber optic spectrometer 42 is demodulated at the cycling frequency of the heater of the micro thermal analyzer 12.

In accordance with one exemplary embodiment of the present invention, the fiber optic cable 52 and infrared light generator 22 deliver a laser beam with a wavelength of 785 nm to the contact area between tip 14 and sample 16. The micro thermal analyzer 12 heats the sample 16 cyclically to a user supplied upper temperature. The micro thermal analyzer 12 may accomplish this heating by applying a known power amplitude and frequency resulting in a temperature fluctuation. The sample 16 may be heated to a temperature of 450° C. As the sample 16 surface 18 is heated and cooled, the sample 16 surface 18 expands and contracts via a thermal lens effect. The laser beam 24 is variably scattered by the expanding and contracting surface 18. The variably scattered laser beam 26 is received by the fiber optic cable 52 and sent to a Kaiser Optical spectrometer 42. The collected signal has an oscillation with a frequency identical to the heating frequency of the micro thermal analyzer 12. A lock in amplifier is present to compare and extract the oscillation of the laser signal to provide the Raman signal of the local area heated by the laser beam 24.

The aforementioned exemplary embodiment provides the user thermal data from the micro thermal analyzer 12, and spectroscopy data from the infrared scattering 26. This information yields insight to the molecular rearrangement of the sample 16 that occurs when the sample 16 is heated.

Figure 3:
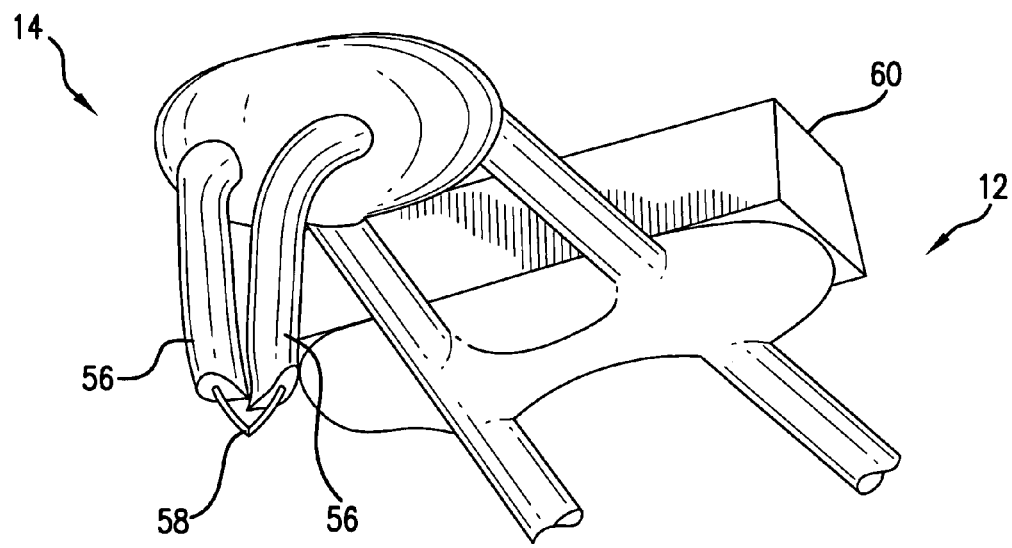
FIG. 3 is a close-up perspective view of a tip of a micro thermal analyzer in accordance with one exemplary embodiment of the present invention.

FIG. 3 shows a close up perspective view of a portion of the micro thermal analyzer 12. The tip 14 includes a pair of wires 56 through which electrical current can be conducted. Current supplied through wires 56 can heat a platinum filament 58 connected therewith in order to heat the surface 18 of sample 16. The micro thermal analyzer 12 also includes a mirror 60 to cause the reflected laser beam 32 to be formed from the laser beam 30.

Figure 4:
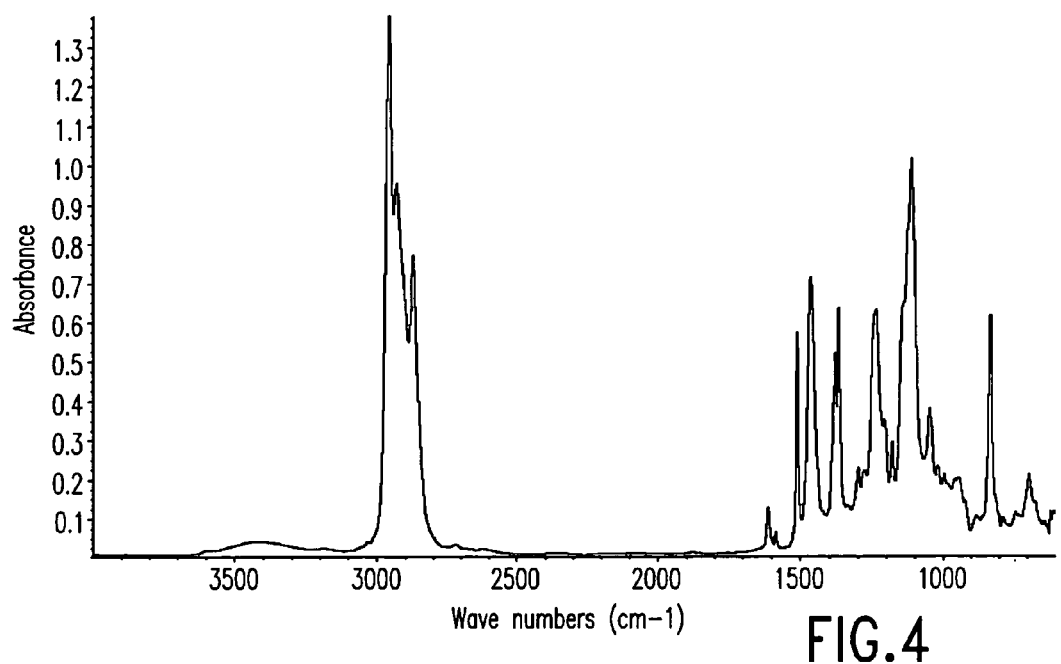
FIG. 4 is a chart of the vibrational spectrum obtained from a sample in accordance with one exemplary embodiment of the present invention.

Demodulation of the infrared scattering 26 by the FTIR spectroscopy 40 yields the complimentary vibrational spectrum of the contact area between tip 14 and the surface 18 of sample 16. The micro thermal analyzer 12 provides the heat capacity, thermal conductivity and enthalpy of any thermal transition at the contact area. Heat collected by the infrared transparent optical fiber 50 is then communicated to the fiber optic spectrometer 40. The heat input is decoded and the output therefrom is the vibrational spectrum of the sample 16. A typical vibrational spectrum generated in accordance with one exemplary embodiment of the present invention is shown in FIG. 4.

In accordance with another exemplary embodiment of the present invention an arrangement as discussed above may include a second optical fiber 50 that is aimed at the contact area between the sample 16 and tip 14. The fiber optical cable 50 collects infrared heat emanating from the locally heated area and communicates this heat to a NEXUS® 670 spectrometer where the heat is modulated and decoded to reveal the vibrational spectrum of the heated region. The vibrational spectrum reveals the molecules present with permanent dipole moments that exist as well as their reaction during the heating. As the area is cyclically heated by the micro thermal analyzer 12, the heat radiated and collected also oscillates. A lock amplifier can be used to extract the steady state signal from the oscillating signal to display the vibrational spectrum. The output from this modification again provides information on the molecular composition of the region and how heating affects the stability of molecules of sample 16.

Additional exemplary embodiments of the present invention are possible in which the atomic force microscope 10 includes a base 20 that allows the sample 16 to be moved in three dimensions with respect to the tip 14. This type of set-up permits different areas of the sample 16 to be scanned by the atomic force microscope 10. The atomic force microscope 10 can be used so that samples 16 of different materials are examined in order to identify the best material for a particular application. For example, the atomic force microscope 10 can be used to identify the best material for a given property such as sorption and desorption. In accordance with one exemplary embodiment, the atomic force microscope 10 is used to determine the best metal alloy for sorbing and desorbing hydrogen, deuterium and tritium gas. The atomic force microscope 10 may be used to quickly determine the ability of a variety of metal alloys to sorb and/or desorb the largest quantity of hydrogen isotopes. Heat energy associated with the desorption process may be regarded as the enthalpy of the sample and can be measured with the micro thermal analyzer 12.

In accordance with certain exemplary embodiments, the micro thermal analyzer 12 is contained in a closed chamber 44 to allow the flow of desired gasses across the micro thermal analyzer 12. This type of arrangement may be beneficial when seeking to determine certain properties of the samples 16 such as the thermal properties of sorption and desorption. FIG. 2 shows a non-reactive gas 46 filling a volume around the sample 16. The sample 16 is positioned under the tip 14 of the micro thermal analyzer 12. A sorbing gas can then be metered into the enclosure 44 at a desired rate while measuring the infrared response, thermal response, and/or the Raman shift response of the sample 16. Also, the evolving chemical reaction of the sample 16 and sorbing gas, if any, can be observed. In a similar manner, samples 16 that desorb a gas or chemical species by applied heat or through a change in the composition of gas surrounding the sample 16 can be analyzed with the atomic force microscope 10.

The atomic force microscope 10 can be arranged to be capable of acquiring topographic data, thermal data, and molecular identification of a sub-micron area of the surface 18 of sample 16. It is to be understood, however, that other exemplary embodiments exist in which fewer than all three of these properties are capable of being determined by the atomic force microscope 10. The disclosed atomic force microscope 10 has a variety of applications. For example, chemical and biological processes on the surface 18 of samples 16 such as implants can be examined. In addition, the phase heterogeneity of surfaces such as secondary phase in blends and corrosion on metallic surfaces can be measured by the atomic force microscope 10. Additional applicability of the atomic force microscope 10 resides in measuring sorbing properties for use in developing coatings for sensors. Further, information obtained from the atomic force microscope 10 can be used in formulating and testing adhesives and other types of coatings.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An atomic force microscope, comprising:
a micro thermal analyzer having a tip, wherein the micro thermal analyzer is configured for obtaining topographic data from a sample;
an infrared light generator configured for directing an infrared beam onto a portion of the sample proximate to the tip of the micro thermal analyzer; and
a Raman spectrometer configured for use in obtaining chemical data from the sampler; and, a fiber optic Fourier transform infrared (FTIR) spectrometer configured for use in obtaining chemical data from the sample.

2. The atomic force microscope as set forth in claim 1, wherein the Raman spectrometer and the fiber optic Fourier transform infrared spectrometer are capable of simultaneously acquiring chemical data from the sample.

3. The atomic force microscope as set forth in claim 1, wherein the Raman spectrometer and the fiber optic Fourier transform infrared (FTIR) spectrometer are in communication with the micro thermal analyzer, and further comprising:
a viewing window located between the sample and an operator of the atomic force microscope, wherein the tip of the micro thermal analyzer is located on the same side of the viewing window as the sample; and
a base onto which the sample is capable of being received, wherein the base and the tip of the micro thermal analyzer are configured for being placed into relative movement with one another so that the tip is configured for relative movement with the sample.

4. The atomic force microscope as set forth in claim 1, wherein the tip of the micro thermal analyzer is configured for having a current passed therethrough so as to generate heat at a portion of the surface proximate to the tip, wherein the fiber optic Fourier transform infrared (FTIR) spectrometer is capable of analyzing the portion of the sample during application of heat by the tip of the micro thermal analyzer so as to yield calorimetric data of the portion of the sample that includes enthalpy and heat capacity.

5. The atomic force microscope as set forth in claim 1, further comprising a microprocessor in communication with the micro thermal analyzer, the Raman spectrometer and the fiber optic Fourier transform infrared (FTIR) spectrometer, wherein the spectrometer is capable of obtaining information from the micro thermal analyzer, the raman spectrometer and the fiber optic Fourier transform infrared (FTIR) spectrometer to yield topographic data, calorimetric data and chemical data of the sample.

6. The atomic force microscope as set forth in claim 1, further comprising an enclosure surrounding the sample being measured and the tip of the micro thermal analyzer, wherein the enclosure is gas tight such that a gas is capable of being introduced into and contained within the enclosure so as to allow the gas to be present at the tip of the micro thermal analyzer and at a portion of the sample being measured.

7. The atomic force microscope as set forth in claim 1, wherein the micro thermal analyzer has a curved cantilever, wherein the tip is located at an end of the curved cantilever of the micro thermal analyzer, wherein the micro thermal analyzer has a mirror, wherein the micro thermal analyzer has a laser and a photo diode array, wherein the laser is configured for directing a laser beam onto the mirror of the micro thermal analyzer such that a reflected laser beam from the mirror strikes the photo diode array, wherein activation of different portions of the photo diode array provides information relative to the location of the tip of the micro thermal analyzer for use in obtaining topographic data from the sample.

8. The atomic force microscope as set forth in claim 1, wherein the micro thermal analyzer is configured for measuring the temperature of the sample due to vibrations of the tip imparted through vibrations of the portion of the sample upon application of the infrared light generator.

9. The atomic force microscope as set forth in claim 1, wherein the tip of the micro thermal analyzer is capable of functioning as a thermocouple in order to obtain calorimetric data from the sample.

10. The atomic force microscope as set forth in claim 1, wherein the chemical data that is obtained is the molecular arrangement of a portion of the sample.

11. An atomic force microscope, comprising:
a micro thermal analyzer having a tip, wherein the micro thermal analyzer is configured for obtaining topographic data from a sample;
an infrared light generator configured for directing an infrared beam onto a portion of the sample proximate to the tip of the micro thermal analyzer;
a spectrometer configured for use in obtaining chemical data from the sample; and
an enclosure surrounding the sample being measured and the tip of the micro thermal analyzer, wherein the enclosure is gas tight such that a gas is capable of being contained within the enclosure so as to allow the gas to be present at the tip of the micro thermal analyzer and at a portion of the sample being measured.

12. The atomic force microscope as set forth in claim 11, wherein the spectrometer is a fiber optic Fourier transform infrared (FTIR) spectrometer.

13. The atomic force microscope as set forth in claim 12, further comprising a raman spectrometer for use in obtaining chemical data from the sample, and wherein the fiber optic Fourier transform infrared (FTIR) spectrometer is configured for use in obtaining temperature data, enthalpy data, heat capacity data, and chemical data from the sample.

14. The atomic force microscope as set forth in claim 13, further comprising a microprocessor in communication with the micro thermal analyzer, the raman spectrometer and the fiber optic Fourier transform infrared (FTIR) spectrometer, wherein the microprocessor is capable of obtaining information from the micro thermal analyzer, the raman spectrometer and the fiber optic Fourier transform infrared (FTIR) spectrometer to yield topographic data, calorimetric data and chemical data of the sample, wherein the calorimetric data includes sorption and desorption of the sample.

15. The atomic force microscope as set forth in claim 13, wherein the raman spectrometer and the fiber optic Fourier transform infrared (FTIR) spectrometer are in communication with the micro thermal analyzer, and further comprising:
a viewing window located between the sample and an operator of the atomic force microscope, wherein the tip of the micro thermal analyzer is located on the same side of the viewing window as the sample; and
a base onto which the sample is capable of being received, wherein the base and the tip of the micro thermal analyzer are configured for being placed into relative movement with one another so that the tip is configured for relative movement with the sample.

16. The atomic force microscope as set forth in claim 11, further comprising a non-reactive gas located in the enclosure.

17. The atomic force microscope as set forth in claim 16, further comprising a sorbing gas that is metered into the enclosure and functions to effect data measurements of the sample taken by the spectrometer.

18. The atomic force microscope as set forth in claim 11, wherein the chemical data that is obtained is the molecular arrangement of a portion of the sample.

19. An atomic force microscope, comprising:
a micro thermal analyzer that has a tip located at an end of a curved cantilever, wherein the curved cantilever carries a mirror, wherein the micro thermal analyzer has a laser and a photo diode array, wherein the laser is configured for directing a laser beam onto the mirror of the micro thermal analyzer such that a reflected laser beam from the mirror strikes the photo diode array so as to provide information relative to the location of the tip;
a base onto which a sample for analysis is located;
an infrared light generator configured for directing an infrared beam onto a portion of the sample proximate to the tip of the micro thermal analyzer;
a fiber optic Fourier transform infrared (FTIR) spectrometer configured for sensing infrared light emitted by the sample upon application of the infrared beam, wherein the Fourier transform infrared (FTIR) spectrometer is configured for use in obtaining calorimetric data from the sample;
a laser beam (785 nm) directed onto a portion of the sample surface proximate to the tip of the micro thermal analyzer;
a Raman spectrometer configured for sensing a scattered beam from the sample for use in obtaining chemical data from the sample; and
an enclosure surrounding the sample being measured and the tip of the micro thermal analyzer, wherein the enclosure is gas tight such that a gas is capable of being contained within the enclosure so as to allow the gas to be present at the tip of the micro thermal analyzer and at a portion of the sample being measured;
wherein the atomic force microscope is capable of simultaneously obtaining topographic data of the sample, calorimetric data of the sample that includes enthalpy and heat capacity, and chemical data of the sample that includes molecular structure.

* * * * *